(12) United States Patent
Kramer

(10) Patent No.: US 7,095,492 B2
(45) Date of Patent: Aug. 22, 2006

(54) METHOD AND APPARATUS FOR MEASURING CELL-BY-CELL HEMOGLOBIN

(75) Inventor: Donald L. Kramer, Boca Raton, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 90 days.

(21) Appl. No.: 10/741,458

(22) Filed: Dec. 19, 2003

(65) Prior Publication Data

US 2005/0134833 A1    Jun. 23, 2005

(51) Int. Cl.
*G01N 33/48* (2006.01)
(52) U.S. Cl. .......................... 356/40; 356/39
(58) Field of Classification Search ............... 356/40, 356/39, 41; 600/320, 328
See application file for complete search history.

(56) References Cited

U.S. PATENT DOCUMENTS

| | | | |
|---|---|---|---|
| 4,711,852 A | 12/1987 | Jacobson et al. | |
| 4,735,504 A | 4/1988 | Tycko | |
| 5,194,909 A * | 3/1993 | Tycko | 356/40 |
| 5,492,833 A * | 2/1996 | Rodriguez et al. | 436/63 |
| 6,228,652 B1 | 5/2001 | Rodriguez et al. | |
| 6,393,310 B1 * | 5/2002 | Kuenstner | 600/322 |
| 6,869,569 B1 * | 3/2005 | Kramer | 422/73 |
| 2001/0024800 A1 * | 9/2001 | Garcia-Rubio et al. | 435/7.21 |
| 2003/0030783 A1 * | 2/2003 | Roche et al. | 356/39 |
| 2004/0038413 A1 | 2/2004 | Kramer | |

OTHER PUBLICATIONS

Tycko, D.H., et al., "Flow-cytometric light scattering measurement of red blood cell volume and hemoglobin concentration", *Applied Optics*, vol. 24, No. 9, pp. 1355-1365, May 1, 1985.

* cited by examiner

*Primary Examiner*—Gregory J Toadey, Jr.
*Assistant Examiner*—Roy M. Punnoose
(74) *Attorney, Agent, or Firm*—Warren W. Kurz; Mitchell E. Alter

(57) ABSTRACT

An apparatus and method for directly determining the hemoglobin content (CH) of individual sphered red blood cells and for directly determining the width of the cell hemoglobin distribution of a red blood cell sample. Such apparatus and method monitors the light reflected by individual sphered cells as they are made to pass through an optical flow cell while being irradiated by a suitable source of radiation.

14 Claims, 5 Drawing Sheets

METHOD AND APPARATUS FOR MEASURING CELL-BY-CELL HEMOGLOBIN

BACKGROUND OF THE INVENTION

1. Field of the Invention

This invention relates to improvements in methods and apparatus for measuring the hemoglobin content of individual red blood cells of a whole blood sample. More particularly, this invention relates to a method for measuring a red blood cell's hemoglobin content on the basis of its reflectivity to radiation at a particular wavelength or wavelengths.

2. The Prior Art

In diagnosing various types of anemias and other blood disorders, as well as in the monitoring of medical treatments, it is necessary to evaluate certain properties of an individual's red blood cells. Those properties of red cells that are routinely reported include: the number of red cells per unit volume of blood (i.e., the red blood cell count, or RBC), the volume percentage of red cells in a whole blood sample (referred to as the Packed Cell Volume, or PCV), the amount of hemoglobin per unit volume of whole blood (referred to as the Hemoglobin Concentration, or [Hgb]), the average size of the red cells (Mean Cell Volume, or MCV), the distribution of the red cell sizes (Red Cell Distribution Width, or RDW), the average amount of hemoglobin in each blood cell (Mean Cell Hemoglobin or, MCH), and the average concentration of hemoglobin within the red blood cells as a whole (Mean Cell Hemoglobin Concentration, or MCHC). Of these particular parameters, most hematology analyzers directly measure only three: RBC, [Hgb], and MCV. The other parameters are calculated from the directly measured parameters.

In addition to the above-noted parameters, other red cell parameters are also useful in fully assessing a blood sample to provide an early diagnosis and/or treatment of disease. Red cells of the same blood sample can substantially differ in their hemoglobin content. When a smear of red cells is viewed under a microscope, the amount of hemoglobin in each red cell correlates well with its color; the brighter red in color, the more hemoglobin within the cell. Having knowledge of the statistical distribution of the individual cell hemoglobin concentrations within a population adds significant information concerning the health of a patient. Red cells with decreased hemoglobin concentration are called hypochromic, while red cells with increased hemoglobin concentration are termed hyperchromic. Populations with an increased distribution of hemoglobin concentrations (i.e., a wide disparity of concentrations) are classified as polychromatophilic. Hyperchromic red cells have altered flow properties and have been suggested as the cellular cause of diseases such as sickle cell anemia.

To provide the statistical distribution information noted above, as well as to provide a more accurate determination of the MCH and MCHC parameters, it is known to measure the hemoglobin concentration of a whole blood sample on a cell-by-cell basis. Such measurements are commonly effected by flow cytometric techniques in which the forward light-scattering (FLS) properties, DC volume (V) and/or RF conductivity (C) of individual cells are determined as each cell passes, one-by-one, through a tiny sensing aperture formed in a cytometric flow cell. See, for example, the respective disclosures of U.S. Pat. Nos. 4,735,504 and 5,194,909, both issued to D. H. Tycko, and the commonly assigned U.S. Pat. No. 5,194,909 issued to R. S. Frank et al.

In the '504 patent to Tycko, "sphered" red cells (i.e., red cells that have been treated to render them substantially spherical in shape) are illuminated by a laser beam as they pass single file through the sensing aperture of an optical (transparent) flow cell. The level of forwardly scattered light from each cell is monitored within two angular regions, and an appropriate algorithm is used to determine each cell's hemoglobin concentration and volume on the basis the two light scatter measurements made. In an article entitled "Flow-Cytometric Light Scattering Measurement of Red Blood Cell Volume and Hemoglobin Concentration" by D. H. Tycko, Applied Optics, Vol. 24, No. 9 (1985), it is noted that the optical measurements relating to volume and HC are extremely complex and interrelated, and require a relatively complex and sophisticated optical system to implement. Additionally, this method requires an absolute calibration of the two optical channels which cannot be done by commonly available latex microspheres. Also, it is noted that the light scatter intensities are non-linear functions of both V and HC, and require considerable computing resources.

In the '909 of Tycko, the patentee improves upon the technique described above by measuring the volume of the sphered red blood cells independently from the optical measurement, thereby reducing the optical complexity and computational requirements. Volume is measured by the standard Coulter Principle according to which a change in a low frequency or DC current (caused to pass through the sensing aperture of a flow cell simultaneously with the passage of cells) indicates the size (volume) of the cell passing through the aperture. In both the '504 and '909 patents, the patentee relies on the supposition that the index of refraction of individual cells, which determines the forward light scattering characteristics, is directly related to the hemoglobin concentration of the cells. This supposition, however, is not necessarily true. It is known that at least about 95% of the interior of a red blood cell is a mixture of hemoglobin molecules and water molecules, and the relative proportions of these two molecules is variable; thus the index or refraction, is variable. Likewise, the remaining 5% of the interior volume of the red blood cell is composed mainly of salts which have a large effect on the index or refraction, especially, when the hemoglobin concentration is very low. Never-the-less, Tycko teaches that by determining the index of refraction by measuring the forward light-scatter intensity within a predetermined angular range, and using the volume of the cell as determined by the DC current measurement through the sensing aperture, the hemoglobin concentration of the cell can be computed.

In the '309 patent of Frank and Wyatt, the hemoglobin concentration is determined by a non-optical technique in which changes in DC and RF currents passing through the sensing aperture simultaneously with the passage of the individual red cells are monitored. While the hemoglobin concentration correlates well with the cell's conductivity, the flow cell aperture must be relatively small in cross-section (preferably about 50×50 microns) in order to achieve a readily detectable change in the RF current. This requirement impacts the overall reliability of the device, since the small aperture can be subject to frequent blockage caused by clumps of cells or debris in the system. Another disadvantage of this technique is the requirement that the conductivity of the diluting fluid required in making the measurement be well controlled to achieve reproducible results.

SUMMARY OF THE INVENTION

In view of the foregoing discussion, an object of the present invention is to provide a simpler and more reliable method for determining the hemoglobin concentration of individual red blood cells in a whole blood sample.

According to this invention, it has been discovered that the reflectivity of red cells to radiation at certain wavelengths accurately correlates with the amount of hemoglobin within the cell. Thus, unlike the prior techniques of monitoring forward light scatter within one or more angular ranges, or monitoring changes in an RF current passing through the sensing aperture simultaneously with the cells, the present invention determines the cell-by-cell hemoglobin by monitoring only the light reflected (i.e., back-scattered) from irradiated individual red cells at an appropriate wavelength, i.e., a wavelength at which the hemoglobin content of the cells has a relatively strong effect on the intensity of the reflected light. Preferably, the red cells are sphered prior to analysis and subjected to an oxygen-enriched sphering solution, preferably one containing carbon monoxide, in order to effect substantially uniform and stable oxygenation of the hemoglobin within the cells, whereby the level of reflected light from the red cells is not dependent on the orientation of the red cell in the measurement zone or on the state of oxygenation of the cell at the time the sample is obtained.

Thus, according to a first aspect of the invention, a method for measuring the hemoglobin content of individual red cells in a whole blood sample comprises the steps of: (a) diluting a whole blood sample in a buffer solution; (b) passing the red cells of the diluted sample, one-at-a-time, through an optical interrogation zone; (c) irradiating each red cell as it passes through the optical interrogation zone with a beam of radiation of predetermined wavelength; (d) detecting the level of radiation reflected from each of the irradiated cells within a predetermined angular range; and (e) determining the hemoglobin concentration of each irradiated cell on the basis of the level of reflected radiation detected. Preferably, the buffer solution contains a chemical reagent adapted to render the red cells substantially spherical in shape, and an oxygen-containing gas, preferably carbon monoxide, adapted to diffuse into a red cell and uniformly oxygenate the hemoglobin contents thereof to form a stable compound, e.g., carboxyhemoglobin. According to a second aspect of the invention, an improved apparatus for determining the hemoglobin content of individual red cells is provided. According to a preferred embodiment, such apparatus comprises (a) an optical flow cell defining an optical interrogation zone through which red cells can be made to pass, one cell at a time; (b) an optical system including a laser for producing a beam of radiation of predetermined wavelength, such beam being acting to irradiated each red cell as it passes through the interrogation zone of the optical flow cell; (c) a reflectance detector for detecting the level of radiation reflected from each of the irradiated cells within a predetermined angular range; and (d) computational means for determining the hemoglobin concentration of each irradiated cell on the basis of the level of reflected radiation detected.

The invention and its advantages will become better understood from the ensuing description of preferred embodiments, reference being made to the accompanying drawings in which like reference characters denotes like parts.

DETAILED DESCRIPTION OF PREFERRED EMBODIMENTS

Figure 1:
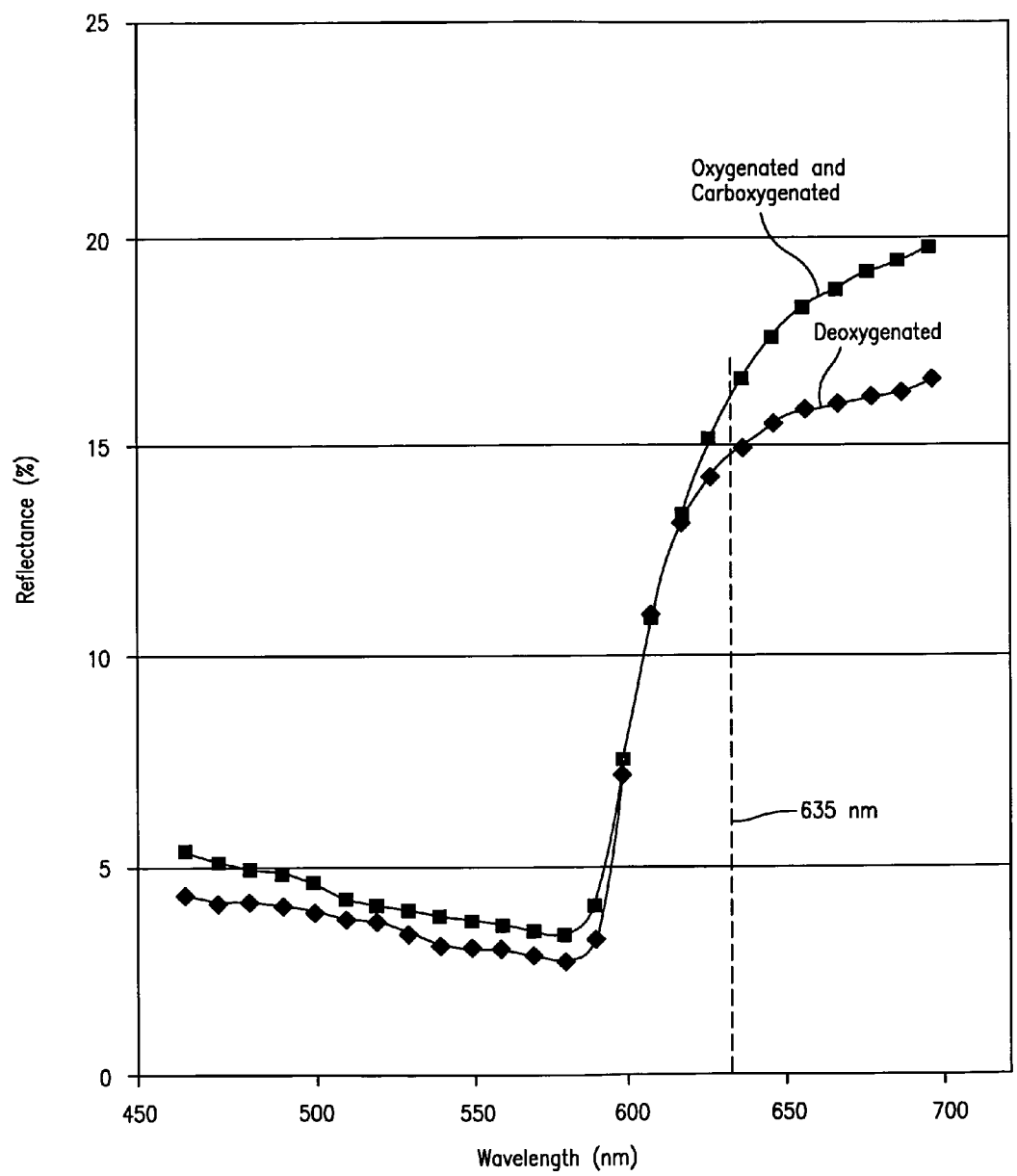
FIG. 1 is a graph illustrating the spectral reflectance characteristics of deoxygenated and carboxygenated whole blood.

In the normal circulation of whole blood through the human body, the constituent blood cells flow in single file through the alveolar capillaries of the lungs. The number of red blood cells (erythrocytes) predominate all other cells by a factor of about 1000:1. In a sample of whole blood, red blood cells exist typically in numbers of about 5 million cells per cubic microliter, although this number varies greatly due to various disease conditions. Within the membrane of each red cell, about 95% of the volume is occupied by water and hemoglobin molecules. As blood circulates through the lungs, the oxygen present in the alveolar capillaries diffuses through the cell membrane and acts to convert virtually all of the hemoglobin within the red cells to a relatively unstable molecular complex known as oxyhemoglobin. During this oxygenation process, the red blood cells become bright red in color. Because the association of the oxygen and hemoglobin molecules within the red cells is relatively "loose" or unstable, the oxygen molecules gradually disassociate from the hemoglobin molecules. This disassociation occurs as the red cells course through the body, as in the normal circulation of blood. Eventually, the oxygen molecules diffuse out of the red cells and back to the tissues for oxidative purposes. As the oxyhemoglobin reduces to hemoglobin, the red cells become dark red in color. In effect, the spectral characteristics of the red cells depends on the instantaneous state of oxygenation. The respective spectral reflectances of oxygenated and deoxygenated whole blood are shown in FIG. 1. As is apparent, the reflectivity of both forms of blood is relatively low in the spectral region below about 600 nm. As the wavelength increase above 600 nm, the reflectivities increase dramatically, and above about 620 nm, the rate of increase in reflectivity of oxygenated blood outpaces that of deoxygenated blood. At 635 nm, where the reflectivity of the blood is at level at which changes in reflectivity can be reliably detected, the difference in reflectivity of oxygenated and deoxygenated blood is substantial. It is at this wavelength or above that red cell reflectance measurements are made in accordance with the invention. Obviously, other wavelengths, preferably longer than 635 nm, can be used for this reflectance measurement, but 635 nm is a preferred wavelength due to the size and availability of solid-state lasers (e.g., gallium-arsenide diode lasers) that emit at this wavelength.

When a blood sample is obtained from a patient, the state of oxygenation of the red cells is unknown and variable. If one desires to quantitate the amount of hemoglobin in the individual red cells of a blood sample on the basis of spectral reflectivity measurements, as is the case of the present invention, it is desirable to have all of the hemoglobin in the sample at the same level of oxygenation, preferably, totally saturated. While one may achieve oxygen-saturated hemoglobin by subjecting the sample to an oxygen atmosphere or solution, the resulting oxyhemoglobin is, as noted above, relatively unstable and short-lived. A preferred approach to stabilizing the hemoglobin in a red blood cell sample is to subject the sample to a carbon monoxide-saturated diluting solution, preferably the same solution used to "sphere" the red cells for analysis. (Note, "sphering" red cells refers to the common practice of treating the cells with reagents (e.g., the detergent, n-dodecyl-n,n-dimethyl-3-ammonio-1-propane sulfonate, or DDAPS) or with other substances known to those skilled in the art that act to convert the biconcave disc-shape of a normal red cell to that of a sphere, whereby the measurement of its properties as it passes through the sensing zone of a flow cell is not altered by its geometric orientation in the sensing zone.) When red cells are subjected to a carbon monoxide-enriched atmosphere, the oxygen molecules of the gas readily bind with the hemoglobin molecules within the red cells (since carbon monoxide has an affinity for hemoglobin about 200 times greater than oxygen) to form carboxyhemoglobin. The latter is a highly stable complex having spectral characteristics, including reflectivity, that are virtually identical to those of oxyhemoglobin. As suggested, converting all the hemoglobin in a blood sample to carboxyhemoglobin is easily accomplished by having a high concentration of carbon monoxide in the solution commonly used to both dilute and sphere the red blood cells in a blood sample.

Figure 2:
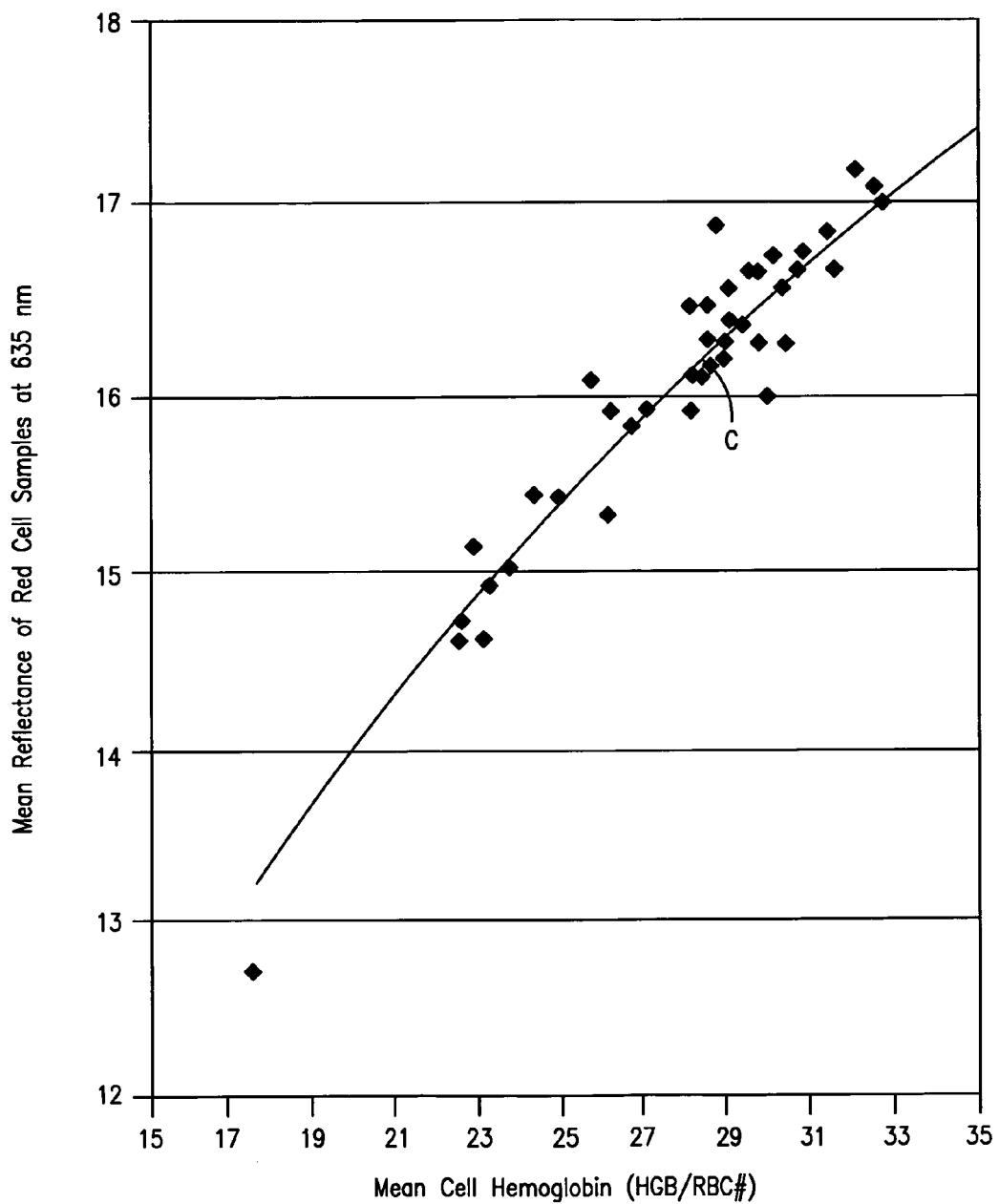
FIG. 2 is a graph illustrating the mean reflectance of different whole blood samples versus the Mean Cell Hemoglobin (MCH) of each sample.
Figure 4:
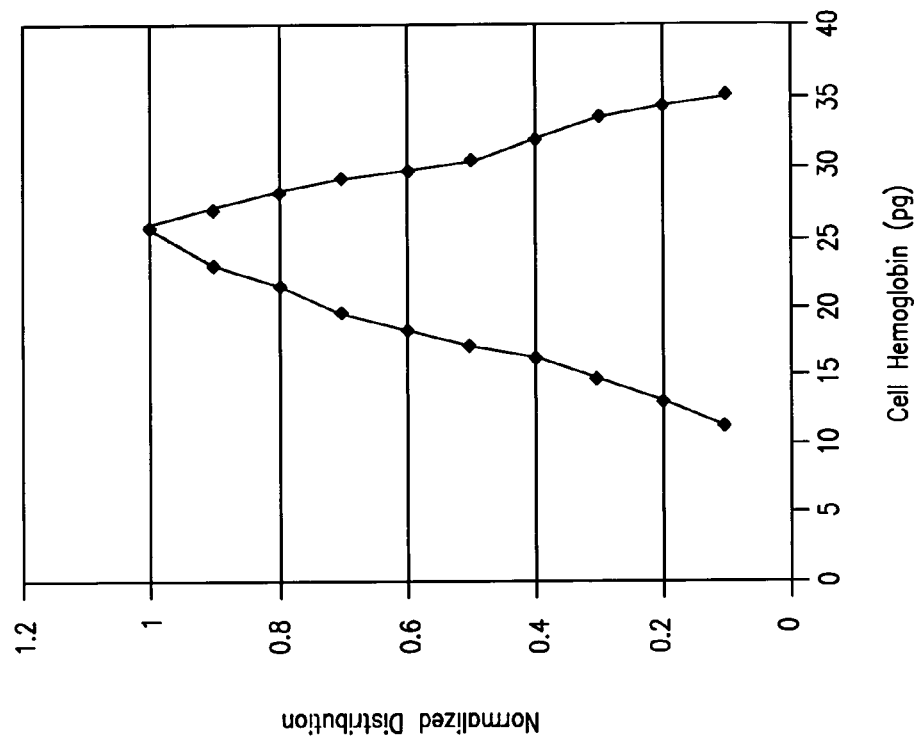
FIGS. 3 and 4 are cell hemoglobin distributions for normal and abnormally low hemoglobin values, respectively.
Figure 3:
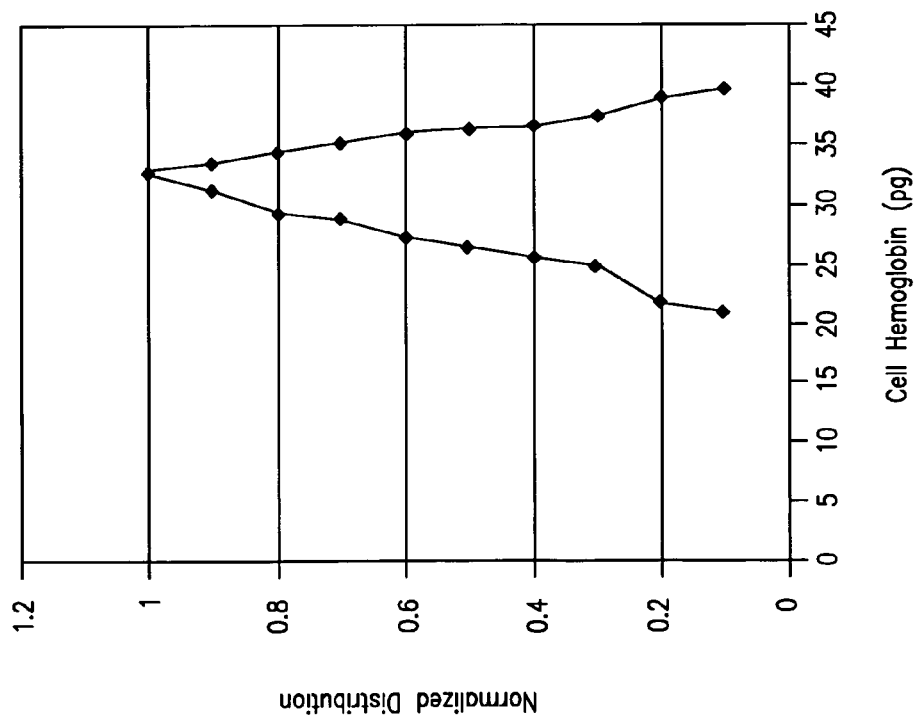

In order to establish the relationship between the reflectance of a red blood cell at 635 nanometers, and the cell's hemoglobin content, a series of experiments were conducted on forty different blood samples. Each of these blood samples was analyzed on a Beckman Coulter Model LH750 Hematology Analyzer to determine the mean cell hemoglobin (MCH) value of each sample. As noted earlier, the MCH is the amount, or mass, of hemoglobin present in an average RBC. The MCH parameter is reported in terms of the mean weight of hemoglobin per cell, in picograms (pg). The MCH is commonly determined by lysing a predetermined volume of a diluted blood sample in order to disperse the red cell hemoglobin into the surrounding diluent and serum, measuring the optical transmission of the lysed sample at a predetermined wavelength, thereby determining the total amount of hemoglobin in that volume of blood, i.e., the [Hgb] parameter, and dividing that total hemoglobin by the number of red blood cells present per unit volume of sample. The result is obviously an average value for each cell. Next, about 20,000 red cells from each of the forty samples were passed through an optical flow cell designed (as described below) to measure the optical reflectance of each individual cell at 635 nm. These cells were sphered in a conventional manner and carboxygenated by bubbling carbon monoxide through the sphering solution for about two minutes. After gathering the reflectance information from the 20,000 individual red blood cells in each sample, the mean reflectance (MR) value of each sample was calculated. Using the values of MCH from the hematology instrument, and the MR values obtained by the cell-by-cell reflectance measurement, a curve C (shown in FIG. 2) is constructed that shows the relationship between these two parameters. In FIG. 2, each data point represents the blood of a different patient. As can be seen from this graph, there exists a mathematical relationship, represented by the best-fit curve, between the mean reflectance values, and the MCH values of the various samples. Knowing this relationship, one can now determine the MCH of any blood sample by determining the mean reflectance of any blood sample and then referring to the curve to determine the MCH. By further examination of each data point for each red blood cell in a sample, the hemoglobin of each individual red blood cell can be also determined. Having measured the reflectivity of an individual red cell, curve C can also be used to determine the cell-by-cell hemoglobin. From the individual cell hemoglobin values, information concerning the red blood cell population can be reported. Further, being able to quantitate the hemoglobin in each red cell of a blood sample, it is possible to report, e.g., in the form of a histogram, the statistical distribution of the cell hemoglobin (CH) in the sample. For example, in the histogram show in FIG. 3, the distribution of cell hemoglobin in a normal sample is shown as being generally symmetrical in shape, with a majority of cells having cell hemoglobin values of between 23 and 39 picograms. In FIG. 4, where an abnormal cell hemoglobin distribution is shown, a large number (about 35%) of cells have a cell hemoglobin in the range of 11 to 22 picograms. Had this blood sample been examined microscopically, a large percentage of the cells would have been reported as hypochromic. Using the invention, the actual percentage of cells having particular cell hemoglobin values can be reported exactly, and the imprecision associated with manual microscopic examination is eliminated.

Figure 5:
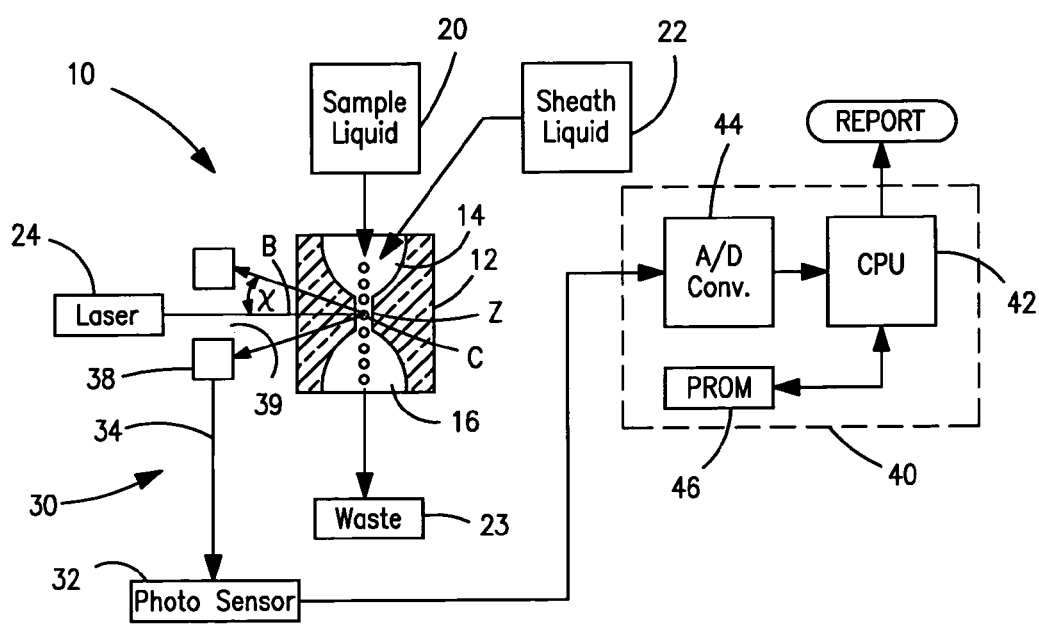
FIG. 5 is a schematic illustration of an electro-optical system embodying the present invention.

FIG. 5 schematically illustrates a preferred flow cytometric apparatus 10 embodying the invention. As described below, apparatus 10 is adapted to determine the cell-by-cell hemoglobin concentration (HGC) of red blood cells on the basis of the optical reflection measurements discussed above. The preferred apparatus of the invention comprises an optical flow cell 12 of the general type disclosed, for example, in the commonly assigned U.S. Pat. No. 6,228,652, issued to C. Rodriguez et al. Flow cell 12 is typically fabricated from quartz, a material that is optically-transparent to a radiation used to irradiate cells passing through the flow cell for the purpose of analyzing the optical characteristics of such cells. Flow cell 12 defines an hour-glass-shaped central opening 14 comprising a pair of opposing cup-shaped chambers, 16, 18, connected by a tiny cell-interrogation zone Z, sometimes referred to as the "sensing aperture." Chamber 16 is adapted to receive a diluted whole blood sample from a sample supply system 20. Note, since the red cells in the diluted whole blood sample outnumber all other cell types by a factor of 1000 to 1, no attempt is made to rid the sample of such other cells, and any abnormal reflectance signal generated by such other cells is simply viewed as an anomaly and ignored. A sheath liquid 22 comprises a hydrodynamic focusing system that serves, in a well known manner, to train a thin stream of sample cells C through the cell-interrogation zone Z so that the red cells of interest are advanced, substantially one-at-a-time, through the central region of zone Z. Upon passing through zone Z, the diluted sample is discharged through flow cell chamber 18 to waste. 23. Preferably, the cell-interrogation zone Z has a square transverse cross-section, measuring about 100 by 100 microns, and an axial length of at least about 75 microns. (Note, the cross-sectional area of zone Z is substantially larger than that required by those cytometric flow cells used to monitor the RF conductivity (C) of cells passing through it. As a result, the construction of the flow cell used in the apparatus of the invention is simplified vis-à-vis such prior art apparatus, and the flow cell yield is significantly greater than those flow cells with the smaller cross-sections.) While passing through the central region of zone Z, each cell C is irradiated by a radiation beam B provided by a continuous-wave laser 24 or the like. For reasons explained below, it is preferred that laser 24 comprises a solid-state laser, e.g. a gallium arsenide diode laser, having an emission line at 635 nanometers. As noted below, this wavelength is chosen because of the spectral reflectance characteristics of hemoglobin.

Figure 6A:
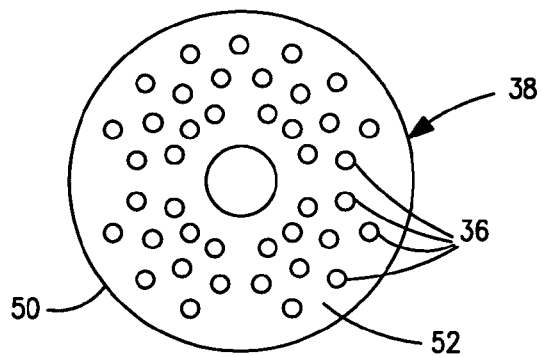
FIGS. 6A–6C illustrate various details of a preferred reflectance detector.
Figure 6B:
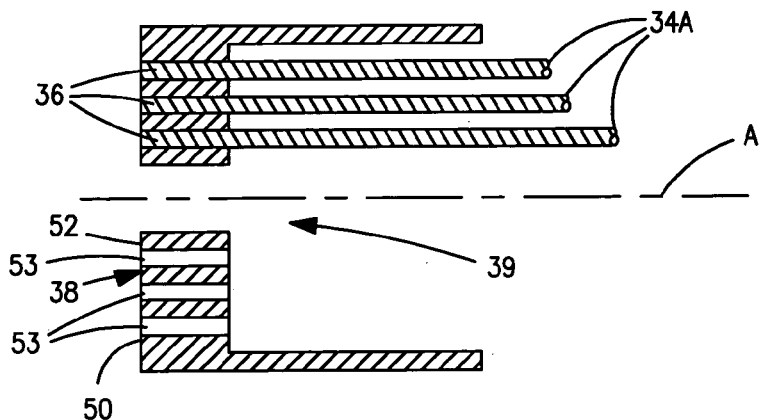
Figure 6C:
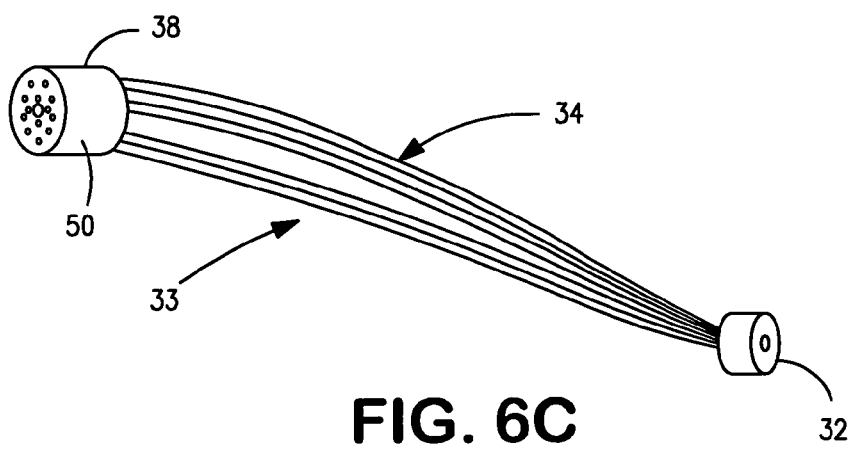

Referring additionally to FIGS. 6A–6C, apparatus 10 further comprises a reflectance detector 30 that is positioned to detect reflected radiation from each of the irradiated cells while it is irradiated within the cell-interrogation zone Z. Reflectance detector 30 comprises a conventional photodetector 32, most preferably a photomultiplier tube (PMT) or other high-gain optical detector that is sensitive to the cell-irradiating radiation, and an optical coupler 33 for concentrating reflected radiation onto the photo-sensitive surface of the photodetector. Preferably, photodetector 32 is optically coupled to the cell-reflected radiation by a bundle of optical fibers 34. The respective input ends 36 of the optical fibers 34A are supported by an optical fiber holder 38 having a central opening 39 through which beam B passes as it propagates between the laser source 24 and the cell interrogation zone Z. The electrical output of photodetector 32 is connected to a signal processor 40 having a central processing unit 42 that serves to compare the digitized signal level (from analog-to-digital converter 44) with a stored signal (embedded in PROM 46) representing the relationship between the cell reflectance and its hemoglobin concentration. Having determined the cell-by-cell hemoglobin of the sample, a report 45 is provided, as discussed below.

As best shown in FIGS. 6B and 6C, the optical coupler 33 is of the type disclosed in the commonly assigned U.S. patent application Ser. No. 10/227,010, filed on Aug. 23, 2002 in the name of D. L. Kramer. Such a device comprises the above-mentioned optical fiber holder 38 which serves to support the light-collecting end portions 36 of each optical fiber 34A so that its respective central axis A is parallel to the axis of the irradiating beam B. Holder 38 comprises a cylindrical sleeve 50, about 12.5 mm. in diameter and 20 mm. in length. One end of the sleeve is closed by a plate 52 in which a series of holes 53 are drilled, each hole acting to support the light-collecting end portion of a single optical fiber. Each optical fiber has a diameter of about 500 microns. Particularly preferred optical fibers are the SI Bare Fiber, sold by Boston Optical Fiber. Preferably, the holes in plate 52 serve to support the light-collecting ends of the optical fibers in three circular arrays, each array being concentrically arranged about the central axis A of the cylindrical sleeve 50 (which coincides with the axis of beam B when the reflectance detector is in use), and each array being at a different radial distance from the beam axis. The light-collecting fiber ends are supported in a common plane, and such plane is spaced from the cell-interrogation zone such that the reflected radiation from the cells is collected within an angular range x of between about 4 degrees and about 10 degrees, measured with respect to the beam axis. The individual fibers need not be arranged in circular arrays, but these arrays serve as a convenience in fabrication. The angles of light collected by the optical fibers can be from about 0.5 degrees to about 25 degrees but, as indicated, the preferred angular range is from about 4 degrees to about 10 degrees. Wider angles of light be utilized, but suffer from reduced intensity. Angle less than 4 degrees are effected by stray light and retro reflection from optical surfaces thereby limiting usefulness.

While the invention has been described with reference to particularly preferred embodiments, it is apparent that various modifications can be made without departing from the spirit and scope of the invention. Such modifications are intended to fall within the scope of the appended claims.

What is claimed is:

1. A method for measuring the hemoglobin content of individual red cells in a whole blood sample comprising the steps of:
    (a) diluting a whole blood sample containing red blood cells in a sphering solution, whereby the red blood cells in the sample are rendered substantially spherical in shape, said solution containing an oxygen-containing gas adapted to bind with the hemoglobin molecules within said red cells to form hemoglobin complexes of substantially uniform reflectivity;
    (b) passing the sphered red cells, one-at-a-time, through an optical interrogation zone;
    (c) irradiating each red cell as it passes through the optical interrogation zone with a beam of radiation of predetermined wavelength;
    (d) detecting the level of radiation reflected from each of the irradiated cells within a predetermined angular range; and
    (e) determining the hemoglobin content of each irradiated cell on the basis of the level of reflected radiation detected.

2. The method as defined by claim 1 wherein said solution contains a detergent adapted to render the shape of the red cells therein substantially spherical.

3. The method as defined by claim 2 wherein said detergent comprises n-dodecyl-n,n-dimethyl-3-ammonio-1-propane sulfonate.

4. The method as defined by claim 1 wherein said gas comprises carbon monoxide.

5. The method of the invention as defined by claim 1 wherein said predetermined wavelength is between 610 nm and 710 nm.

6. The method as defined by claim 1 wherein said wavelength is about 635 mm.

7. A method for measuring the hemoglobin content of individual red cells in a whole blood sample comprising the steps of:
    (a) diluting a whole blood sample containing red blood cells in a sphering solution, whereby the red blood cells in the sample are rendered substantially spherical in shape;
    (b) passing the sphered red cells, one-at-a-time, through an optical interrogation zone;
    (c) irradiating each red cell as it passes through the optical interrogation zone with a beam of radiation of predetermined wavelength;
    (d) detecting the level of radiation reflected from each of the irradiated cells within a predetermined angular range; and
    (e) determining the hemoglobin content of each irradiated cell on the basis of the level of reflected radiation detected, said determining step being effected by storing in a computer memory a relationship between the Mean Cell Hemoglobin of various different whole blood samples and the Mean Cell Reflectance of said samples to irradiating radiation at said predetermined wavelength, and by determining the cell hemoglobin based on the measured reflectivity of each cell and said stored relationship.

8. Apparatus for determining the hemoglobin content of individual red cells in a whole blood sample, said apparatus comprising:

(a) an optical flow cell defining an optical interrogation zone through which red cells can be made to pass, one cell at a time;
(b) an optical system including a laser for producing a beam of radiation of predetermined wavelength, such beam being directed to irradiated each red cell as it passes through the interrogation zone of the optical flow cell;
(c) a reflectance detector for detecting the level of radiation reflected from each of the irradiated cells within a predetermined angular range, said reflectance detector comprising a plurality of optical fibers having light-collecting ends positioned to receive radiation reflected from said irradiated red cells, and light-discharge ends positioned adjacent a high-gain photodetector; and
(d) computational means for determining the hemoglobin content of each irradiated cell on the basis of the level of reflected radiation detected.

9. The apparatus as defined by claim 8 wherein said light-collecting ends of said optical fibers are arranged in a plurality of circular arrays concentrically arranged with respect to the irradiating beam of radiation.

10. The apparatus as defined by claim 8 wherein said high-gain photodetector comprises a photomultiplier tube.

11. The apparatus as defined by claim 8, wherein said predetermined angular range is between about 4 degrees and 10 degrees, measured with respect to the axis of propagation of said beam of radiation.

12. Apparatus for determining the hemoglobin content of individual red cells in a whole blood sample, said apparatus comprising:
(a) an optical flow cell defining an optical interrogation zone through which red cells can be made to pass, one cell at a time;
(b) an optical system including a laser for producing a beam of radiation of predetermined wavelength, such beam being directed to irradiated each red cell as it passes through the interrogation zone of the optical flow cell;
(c) a reflectance detector for detecting the level of radiation reflected from each of the irradiated cells within a predetermined angular range; and
(d) computational means for determining the hemoglobin content of each irradiated cell on the basis of the level of reflected radiation detected, said computational means comprising (i) a memory in which there is stored a relationship between the Mean Cell Hemoglobin of various different whole blood samples and the Mean Cell Reflectance of said samples to irradiating radiation at said predetermined wavelength, and (ii) means for determining the cell hemoglobin of each irradiated red cell based on the measured reflectivity of each red cell and said stored relationship.

13. A method for measuring the hemoglobin content of individual red cells in a whole blood sample comprising the steps of:
(a) diluting a whole blood sample containing red blood cells in a sphering solution, whereby the red blood cells in the sample are rendered substantially spherical in shape;
(b) passing the sphered red cells, one-at-a-time, through an optical interrogation zone;
(c) irradiating each red cell as it passes through the optical interrogation zone with a beam of radiation of predetermined wavelength;
(d) detecting the level of radiation reflected from each of the irradiated cells within a predetermined angular range; and
(e) determining the hemoglobin content of each irradiated cell on the basis of the level of reflected radiation detected.

14. Apparatus for determining the hemoglobin content of individual red cells in a whole blood sample, said apparatus comprising:
(a) an optical flow cell defining an optical interrogation zone through which red cells can be made to pass, one cell at a time;
(b) an optical system including a laser for producing a beam of radiation of predetermined wavelength, such beam being directed to irradiated each red cell as it passes through the interrogation zone of the optical flow cell;
(c) a reflectance detector for detecting the level of radiation reflected from each of the irradiated cells within a predetermined angular range; and
(d) computational means for determining the hemoglobin content of each irradiated cell on the basis of the level of reflected radiation detected.

* * * * *